(12) United States Patent
Nakajima et al.

(10) Patent No.: US 8,551,364 B2
(45) Date of Patent: Oct. 8, 2013

(54) PROCESS FOR INHIBITING POLYMERIZATION OF AN AROMATIC VINYL COMPOUND

(75) Inventors: Junichi Nakajima, Yokkaichi (JP); Seiji Tanizaki, Yokkaichi (JP)

(73) Assignee: Hakuto Co., Ltd., Tokyo (JP)

( * ) Notice: Subject to any disclaimer, the term of this patent is extended or adjusted under 35 U.S.C. 154(b) by 0 days.

(21) Appl. No.: 13/528,290

(22) Filed: Jun. 20, 2012

(65) Prior Publication Data

US 2012/0264985 A1  Oct. 18, 2012

Related U.S. Application Data

(62) Division of application No. 12/224,748, filed as application No. PCT/JP2007/055968 on Mar. 23, 2007, now Pat. No. 8,246,858.

(30) Foreign Application Priority Data

Mar. 24, 2006 (JP) .................................. 2006-082571
Mar. 24, 2006 (JP) .................................. 2006-082572

(51) Int. Cl.

| C09K 3/00 | (2006.01) |
|---|---|
| C09K 15/00 | (2006.01) |
| C09K 15/04 | (2006.01) |
| C09K 15/16 | (2006.01) |
| C09K 15/22 | (2006.01) |
| C09K 15/06 | (2006.01) |
| C07D 295/00 | (2006.01) |
| C07D 405/00 | (2006.01) |
| C07D 409/00 | (2006.01) |
| C07D 207/00 | (2006.01) |
| C07D 207/04 | (2006.01) |
| C07D 295/04 | (2006.01) |
| C08F 2/38 | (2006.01) |

(52) U.S. Cl.
USPC ...... 252/403; 252/182.29; 252/397; 252/399; 252/401; 252/405; 252/407; 548/518; 548/526; 548/530; 548/577; 526/82

(58) Field of Classification Search
USPC .................... 252/405, 182.29, 397, 399, 401, 252/403, 407; 526/82; 548/518, 526, 530, 548/577

See application file for complete search history.

(56) References Cited

U.S. PATENT DOCUMENTS

| 2,812,329 | A | * | 11/1957 | Reusser et al. ................ 546/351 |
|---|---|---|---|---|
| 3,210,419 | A | | 10/1965 | McConnell |
| 4,425,223 | A | | 1/1984 | Miller |
| 4,654,450 | A | | 3/1987 | Miller |
| 5,157,175 | A | | 10/1992 | Lewis et al. |
| 5,824,829 | A | | 10/1998 | Maeda et al. |
| 2004/0147797 | A1 | | 7/2004 | Tanizaki et al. |
| 2006/0122341 | A1 | * | 6/2006 | Kosover et al. ................ 526/82 |

FOREIGN PATENT DOCUMENTS

| JP | 63316745 A | 12/1988 |
|---|---|---|
| JP | 01165534 A | 6/1989 |
| JP | 06166636 A | 6/1994 |
| JP | 08034748 A | 2/1996 |
| JP | 2003-277413 | 10/2003 |

* cited by examiner

*Primary Examiner* — Harold Pyon
*Assistant Examiner* — Tanisha Diggs
(74) *Attorney, Agent, or Firm* — Flynn, Thiel, Boutell & Tanis, P.C.

(57) ABSTRACT

A process for inhibiting polymerization of an aromatic vinyl compound during the stage of producing, purifying, storing or transporting the aromatic vinyl compound which not only inhibits an initial polymerization but also inhibits polymerization efficiently over a long period of time and which is excellent in handleability. The process involves the step of adding a nitrogenous aromatic compound in combination with a sulfonic acid compound to the aromatic vinyl compound during the production, purification, storage of transportation thereof.

6 Claims, No Drawings

PROCESS FOR INHIBITING POLYMERIZATION OF AN AROMATIC VINYL COMPOUND

This is a divisional of prior U.S. application Ser. No. 12/224,748, now U.S. Pat. No. 8,246,858, filed Feb. 2, 2009 which was the National Stage of International Application No. PCT/JP2007/055968, filed Mar. 23, 2007, which claims priority from JP 2006-082571, filed Mar. 24, 2006 and JP 2006-082572, filed Mar. 24, 2006.

TECHNICAL FIELD

The present invention relates to a process for inhibiting polymerization of an aromatic vinyl compound or of a process fluid containing it during the stage of producing, purifying, storing or transporting the aromatic vinyl compound.

BACKGROUND ART

Among aromatic vinyl compounds, styrene especially is an industrially very important compound as a raw material for preparing polystyrene, synthetic rubber, ABS resin, etc. and has been industrially manufactured in a large amount.

In general, an aromatic vinyl compound is extremely susceptible to polymerization so that it easily undergoes polymerization under an influence of the heat generated in its preparation or purification stage, thereby causing problems of lowering the yield of the monomeric aromatic vinyl compound and, further, of forming soil (fouling) in the facilities involved to induce trouble in operating the facilities. As the countermeasure taken hitherto, a process wherein a certain polymerization inhibitor is added to process fluid containing an aromatic vinyl compound has been proposed and practically carried out. For example, there have been proposed a process employing phenols, nitrosophenols and/or nitrophenols (e.g. patent literature 1), one employing piperidine-1-oxyls (e.g. patent literature 2), one employing nitrophenols together with piperidine-1-oxyls) (e.g. patent literature 3), one employing an alkylsulfonic acid in combination with a dialkylhydroxylamine (e.g. patent literature 4), one employing a phosphoric acid ester and an alkylsulfonic acid in combination (e.g. patent literature 5), one adding phenol-, amine- and/or nitroso-related polymerization inhibitors together with dodecylbenzenesulfonic acid or its salt in order to suppress an increase in viscosity during an olefin preparation process (e.g. patent literature 6), and one adding a quinone-, hydroquinone- or nitroso-related polymerization inhibitor, or an amine-related polymerization inhibitor such as phenylenediamine together with dodecylbenzenesulfonic acid or its salt for preventing the formation of fouling in stage treating a vinyl compound (e.g. patent literature 7). Among them, especially 2,4-dinitrophenol (DNP) and 2,6-dinitro-4-methylphenol, 2,4-dinitro-6-sec-butylphenol (DNBP), which are nitrophenol compounds, have been often used as the polymerization inhibitors for the aromatic vinyl compound. However, these chemical agents show a tendency to gradually decrease their inhibitory power toward the polymerization reaction and necessitate a strict care in handling them because they belong to toxic substances. Accordingly, there has been strongly desired a process by which the effect of these chemical agents on polymerization-inhibition may be maintained and the amount used of them may be reduced.

Patent literature 1: JP 63-316745 A
Patent literature 2: JP 1-165534 A
Patent literature 3: JP 6-166636 A
Patent literature 4: U.S. Pat. No. 4,654,450 specification
Patent literature 5: U.S. Pat. No. 4,425,223 specification
Patent literature 6: JP 7-166152 A
Patent literature 7: JP 8-34748 A

DISCLOSURE OF THE INVENTION

Subject Matter to be Solved by the Invention

So, an object of the present invention is to provide a process for inhibiting polymerization of an aromatic vinyl compound during the stage of producing, purifying, storing or transporting of the aromatic vinyl compound which is capable of efficiently inhibiting polymerization not only in an initial stage but also over a long period of time and which is excellent in handleabilily.

Means for Solving the Subject Matter

As a result of having studied about characteristic properties of the polymerization reaction of an aromatic vinyl compound in detail, the present inventors have found that when a specific nitrogenous aromatic compound and a specific sulfonic acid compound were employed in combination, superior synergic polymerization-inhibiting effect may be obtained in comparison with the effect obtained when each of them was employed singly, and have completed the present invention.

That is, the invention is a process for inhibiting polymerization of an aromatic vinyl compound which comprises adding (A) at least one member selected from the nitrogenous aromatic compounds represented by the following general formulae (I), (II), (III) and (IV) in combination with (B) a sulfonic acid compound represented by the following general formula (V) during the stage producing, purifying, storing or transporting the aromatic vinyl compound

[Chemical formula 1]

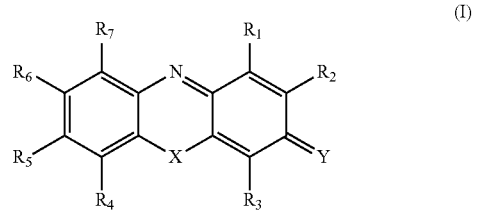

(I)

wherein $R_1 \sim R_7$ represent independently hydrogen, hydroxyl group, a straight or branched chain alkyl group having from 1 to 12 carbon atoms, a straight or branched chain alkenyl group having from 2 to 12 carbon atoms, an aryl group having from 6 to 14 carbon atoms, an amino group, a mono- or di-alkyl amino group whose alkyl group is a straight or branched chain alkyl having from 1 to 12 carbon atoms, a mono- or di-aryl amino group whose aryl group has from 6 to 12 carbon atoms, a formyl group, a carboxyl group, a carbamoyl group and a sulfonic acid residue, adjacent two substituent groups may take an alicyclic or an aromatic cyclic structure together, X represents oxygen or sulfur atom and Y represents oxygen or nitrogen atom

[Chemical formula 2]

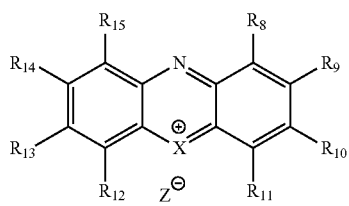

(II)

wherein $R_8 \sim R_{15}$ represent independently hydrogen, hydroxyl group, a straight or branched chain alkyl group having from 1 to 12 carbon atoms, a straight or branched chain alkenyl group having from 2 to 12 carbon atoms, an aryl group having from 6 to 14 carbon atoms, an amino group, a mono- or di-alkyl amino group whose alkyl group is a straight or branched chain alkyl having from 1 to 12 carbon atoms, a mono- or di-aryl amino group whose aryl group has from 6 to 12 carbon atoms, a formyl group, a carboxyl group, a carbamoyl group and a sulfonic acid residue, adjacent two substituent groups may take an alicyclic or an aromatic cyclic structure together, Y represents oxygen or nitrogen atom, X represents oxygen or sulfur atom and Z represents formic acid ion, acetic acid ion, propionic acid ion, sulfuric acid ion, chloride ion and nitric acid ion

[Chemical formula 3]

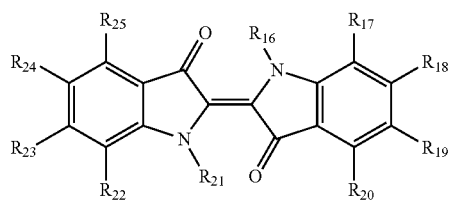

(III)

wherein $R_{16} \sim R_{25}$ represent independently hydrogen, hydroxyl group, a straight or branched chain alkyl group having from 1 to 12 carbon atoms, a straight or branched chain alkenyl group having from 2 to 12 carbon atoms, an aryl group having from 6 to 14 carbon atoms, an amino group, mono- or di-alkyl amino group whose alkyl group is a straight or branched chain alkyl having from 1 to 12 carbon atoms, a mono- or di-aryl amino group whose aryl group has from 6 to 12 carbon atoms, a formyl group, a carboxyl group, a carbamoyl group and a sulfonic acid residue, and adjacent two substituent groups may take an alicyclic or an aromatic cyclic structure together.

[Chemical formula 4]

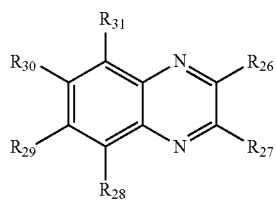

(IV)

wherein $R_{26} \sim R_{31}$ represent independently hydrogen, hydroxyl group, a straight or branched chain alkyl group having from 1 to 12 carbon atoms, a straight or branched chain alkenyl group having from 2 to 12 carbon atoms, an aryl group having from 6 to 14 carbon atoms, an amino group, an amino group substituted by at least one of straight or branched chain alkyl group having from 1 to 12 carbon atoms, an amino group substituted by at least one of aryl group having from 6 to 14 carbon atoms, and each of the two substituent groups of $R_{26}$ and $R_{27}$, of $R_{28}$ and $R_{29}$, of $R_{29}$ and $R_{30}$, and of $R_{30}$ and $R_{31}$ may bond together to form an alicyclic or an aromatic cyclic structure.

[Chemical formula 5]

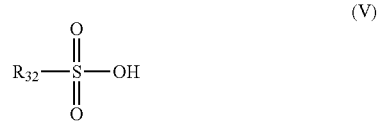

(V)

wherein $R_{32}$ represents hydroxyl group, a straight or branched chain alkyl group having 1-32 carbon atoms, an alkylphenyl group wherein the alkyl group is a straight or branched chain one having 1-32 carbon atoms or an alkyl-naphthyl group wherein the alkyl group is a straight or branched chain alkyl having 1-32 carbon atoms.

The invention is also the process for inhibiting polymerization of an aromatic vinyl compound, wherein the nitrogenous aromatic compound represented by the general formula (I) in the before-described (A) component is at least one member selected from methylene violet, resorufin and phenothiazine-3-oxide.

The invention is also the process for inhibiting polymerization of an aromatic vinyl compound, wherein the nitrogenous aromatic compound represented by the general formula (II) in the before-described (A) component is at least one member selected from cresyl violet, thionine and methylene blue.

The invention is also the process for inhibiting polymerization of an aromatic vinyl compound, wherein the nitrogenous aromatic compound represented by the general formula (III) in the before-described (A) component is indigo and/or indigo carmine.

The invention is also the process for inhibiting polymerization of an aromatic vinyl compound, wherein the nitrogenous aromatic compound represented by the general formula (IV) in the before-described (A) component is at least one member selected from the group consisting of phenazine, 2-methylphenazine, 2-ethylphenazine, quinoxaline, 2-methylquinoxaline, 2-phenylquinoxaline, 3-amino-7-hydroxyl-2-methylphenazine and tetrabenzo[a,c,h,j]phenazine.

The invention is also the process for inhibiting polymerization of an aromatic vinyl compound, wherein the sulfonic acid compound represented by the general formula (V) in the before-described (B) component is at least one member selected from toluenesulfonic acid, xylenesulfonic acid, cumenesulfonic acid, dodecylbenzene-sulfonic acid, pentadecylbenzenesulfonic acid and dinonyl-naphthalenesulfonic acid.

The invention is also the process for inhibiting polymerization of an aromatic vinyl compound, wherein the nitrogenous aromatic compound of the (A) component and the sulfonic acid compound of the (B) component are added in combination in the range of 5:95 to 95:5 by weight ratio.

Effect of the Invention

By the present invention, the polymerization of an aromatic vinyl compound or of a process fluid containing it may be efficiently inhibited and the effect may be kept for a long period of time thereby ensuring an advantage that the amount of fouling generated in the facilities involved may be minimized to attribute greatly to the safe operation of the facilities and to the reduction in the production cost.

THE BEST MODE FOR CARRYING OUT THE INVENTION

The stages which become a target for inhibiting the polymerization in the present invention are: production stage of an aromatic vinyl compound, purification stage of the produced aromatic vinyl compound and storage stage of the purified aromatic vinyl compound, and they include attachment devices or equipment which are in contact with process liquid containing aromatic vinyl compound, and further circulation and recovery systems containing them. Specifically, a dehydrogenation reaction column or synthetic reaction column of an alkyl aromatic compound, discharge line or recovery and circulating line of the reaction product after the reaction in the production stage of an aromatic vinyl compound, piping for feeding an aromatic vinyl compound to the purification column, preheating line and cooling line and further circulating line in the purification stage, charge tank, storage tank, transfer tank and transport tank and further transfer lines thereof and so on in the storage stage are taken out.

As the aromatic vinyl compound, styrene and styrene derivatives having a polymerizable vinyl group such as an alkylstyrene whose alkyl has 1-10 carbon atoms, α-alkylstyrene where phenyl group or alkyl group each having 1-10 carbon atoms is located at the α-position, β-alkylstyrene where phenyl group or alkyl group each having 1-10 carbon atoms is located at the β-position and the like are taken. Specifically, styrene, methylstyrene (ortho form, meta form, para form and mixtures thereof), ethylstyrene (ortho form, meta form, para form and mixtures thereof), propylstyrene (ortho form, meta form, para form and mixtures thereof), butylstyrene (ortho form, meta form, para form and mixtures thereof), octylstyrene (ortho form, meta form, para form and mixtures thereof), nonylstyrene (ortho form, meta form, para form and mixtures thereof), decylstyrene (ortho form, meta form, para form and mixtures thereof), α-methylstyrene (2-phenylpropene), 1-phenyl-1-propene (β-methyl-styrene: cis form, trans form and mixtures thereof), 2-phenyl-2-butene (cis form, trans form and mixtures thereof), stilbene (cis form, trans form and mixtures thereof) and the like are taken.

The nitrogenous aromatic compounds represented by the general formulae (I)-(IV) as the (A) component which may be used for inhibiting the polymerization of these aromatic vinyl compounds have cyclic structure together with hetero atom. Among these compounds, compounds represented by the general formulae (I) and (II) are polycyclic imino compounds. Each of $R_1$~$R_7$ in the general formula (I) and each of $R_8$~$R_{15}$ in the general formula (II) represent independently hydrogen, hydroxyl group, a straight or branched chain alkyl group having from 1 to 12 carbon atoms, a straight or branched chain alkenyl group having from 2 to 12 carbon atoms, an aryl group having from 6 to 14 carbon atoms, mono- or di-alkyl amino group whose alkyl group is a straight or branched chain alkyl having from 1 to 12 carbon atoms, mono- or di-aryl amino group whose aryl group has from 6 to 12 carbon atoms, a formyl group, a carboxyl group, a carbamoyl group and a sulfonic acid residue. Also, adjacent two substituent groups may take an alicyclic or an aromatic cyclic structure together. X represents oxygen or sulfur atom and Y represents oxygen or nitrogen atom. Z is not particularly restricted so long as it is an anion which forms a salt with a polycyclic imino compound. Usually, organic acid anions such as formic acid ion, acetic acid ion, propionic acid ion, inorganic acid ions such as chloride ion, sulfuric acid ion and nitric acid ion may be exemplified. Specific examples of a polycyclic imino compound include resorufin, methylene violet, phenothiazine-3-oxide, cresyl violet acetate, thionine and methylene blue.

Also, in the indigo compound represented by the general formula (III), each of $R_{16}$~$R_{25}$ in the formula represents independently hydrogen, hydroxyl group, a straight or branched chain alkyl group having from 1 to 12 carbon atoms, a straight or branched chain alkenyl group having from 2 to 12 carbon atoms, an aryl group having from 6 to 14 carbon atoms, an amino group, mono- or di-alkyl amino group whose alkyl group is a straight or branched chain one having from 1 to 12 carbon atoms, a mono- or di-aryl amino group whose aryl group has from 6 to 12 carbon atoms, a formyl group, a carboxyl group, a carbamoyl group and a sulfonic acid residue, and adjacent two substituent groups may take an alicyclic or an aromatic cyclic structure together. Examples of an indigo compound include indigo, indigo carmine and the like. Although certain tautomer exists in these compounds, the indigo compounds include the tautomer.

Also, in the compound represented by the general formula (IV), each of $R_{26}$~$R_{31}$ in the formula represents independently hydrogen, hydroxyl group, a straight or branched chain alkyl group having from 1 to 12 carbon atoms, a straight or branched chain alkenyl group having from 2 to 12 carbon atoms, an aryl group having from 6 to 14 carbon atoms, an amino group, an alkyl substituted amino group where at least one of straight or branched chain alkyl group having from 1 to 12 carbon atoms is located, an aryl-substituted amino group where at least one of aryl group having from 6 to 14 carbon atoms is located, and each of the two substituent groups of $R_{26}$ and $R_{27}$, of $R_{28}$ and $R_{29}$, of $R_{29}$ and $R_{30}$, and of $R_{30}$ and $R_{31}$ may bond together to form an alicyclic or an aromatic cyclic structure. As the specific compound, phenazine, 2-methylphenazine, 2-ethylphenazine, quinoxaline, 2-methyl-quinoxaline, 2-phenylquinoxaline, 3-amino-7-hydroxyl-2-methylphenazine, tetrabenzo[a,c,h,j]phenazine and the like are taken.

In the sulfonic acid compound represented by the general formula (V) as the (B) component which may be used in combination with these nitrogenous aromatic compounds represented by the general formulae (I)-(IV) as the (A) component, $R_{32}$ in the formula represents hydroxyl group, a straight or branched chain alkyl group having 1-32 carbon atoms, an alkyl substituted phenyl group or an alkyl substituted naphthyl group where at least one straight or branched chain alkyl group having 1-32 carbon atoms is located. One or more kinds of these sulfonic acid compounds may be selected. Examples of a sulfonic acid compound include sulfuric acid, toluenesulfonic acid, xylenesulfonic acid, cumenesulfonic acid, dodecylbenzene sulfonic acid, pentadecylbenzenesulfonic acid, dinonylnaphthalene-sulfonic acid and the like. Especially pentadecylbenzenesulfonic acid and dodecylbenzene sulfonic acid are preferred from the standpoint of view of their solubility toward aromatic vinyl compound, cost and so on.

The mixture ratio of the nitrogenous aromatic compound of the (A) component to the sulfonic acid compound of the (B) component is a matter to be adequately determined depending on the intended extent in the polymerization inhibition of the aromatic vinyl compound and hence cannot be determined as a rule. However, the nitrogenous aromatic compound of the (A) component and the sulfonic acid compound of the (B) component are added to the targeted aromatic vinyl compound in the range of generally 95:5 to 5:95, preferably 80:20 to 20:80, more preferably 70:30 to 30:70 by weight ratio.

The amount of the nitrogenous aromatic compound of the (A) component and of the sulfonic acid compound of the (B) component to be added to the targeted stage may be varied depending on the condition in the target stage, the degree required for the polymerization inhibition and so on and hence it cannot be determined as a rule. However, the nitrogenous aromatic compound of the (A) component is added in the range of generally 1-3000 ppm, preferably 10-2000 ppm, more preferably 100-1000 ppm to the targeted aromatic vinyl compound while the sulfonic acid compound of the (B) component is added in the range of generally 1-3000 ppm, preferably 10-2000 ppm, more preferably 100-1000 ppm thereto. The amount added of the respective components are values found as the proper range for exerting the polymerization-inhibiting effect toward the targeted aromatic vinyl compound. When they are smaller than this range, the effect is not sufficient. Also, when they are greater than the this range, the effect is sufficient but in some case it does not become great relative to the increase in the added amount and it is not preferable from the economical aspect.

The place in the target stage at which the nitrogenous aromatic compound of the (A) component and of the sulfonic acid compound of the (B) component are added in the present invention is not particularly restricted, they are added to the upstream process over the place at which an aromatic vinyl compound undergoes polymerization to cause the problem as fouling. For example, styrene is generally manufactured by a dehydrogenation reaction of ethyl benzene, and the formed styrene is continuously separated from the unreacted ethyl benbenzene by distillation, and therefore the nitrogenous aromatic compound and the sulfonic acid compound are supplied to the distillation columns after the dehydrogenation reaction of ethyl benzene has been conducted.

Although the means to be applied when the nitrogenous aromatic compound of the (A) component and the sulfonic acid compound of the (B) component are added to the targeted stage in the present invention is not particularly restricted, such a suitable means may be selected as they may be added to the specific place at one stroke or otherwise they may be separately added to some places on portions. In this case, although each of the before-described (A) and (B) components may be added separately, it is practically convenient that both the components are added in a proper mixture ratio and in a state dissolved in the same liquid as the process liquid, for example in case of being applied to styrene, in a state dissolved in ethyl benzene or crude styrene.

In the present invention, no limitation shall be imposed on that any other known polymerization inhibitor than the before described (A) and (B) components is used in combination in the range not impairing the effect of the present invention.

Working Example

The present invention is illustrated in more details by the working example but it is not restricted to the following working examples.

Compounds Used for Evaluation (A) Component (Nitrogenous Aromatic Compound)

A-1: methylene violet (a product of Tokyo Kasei Kogyo Co., Ltd.)

A-2: resorufin (a product of Tokyo Kasei Kogyo Co., Ltd.)

A-3: cresyl violet (a product of Aldrich Chemical Company)

A-4: thionine (a product of Aldrich Chemical Company)

A-5: methylene blue (a product of Tokyo Kasei Kogyo Co., Ltd.)

A-6: indigo

A-7: indigo carmine

A-8: quinoxaline

A-9: 1-methyl quinoxaline

A-10: phenazine

A-11: 3-amino-7-hydroxyl-2-methylphenazine

A-12: tetrabenzo[a,c,h,j]phenazine (B) Component (Sulfonic Acid Compound)

B-1: dodecylbenzenesulfonic acid

B-2: pentadecylbenzenesulfonic acid

B-3: xylenesulfonic acid

B-4: cumenesulfonic acid

B-5: p-toluenesulfonic acid

B-6: methansulfonic acid

B-7: sulfuric acid (98%)

(Others)

DNBP: 2,4 dinitro-6-sec-butyl phenol

H-TEMPO: 4-hydroxy-2,2,6,6-tetramethylpiperidine-1-oxyl

Polymerization-Inhibiting Test-1

100 Grams of styrene monomer was placed in a four-necked separable flask equipped with a reflux condenser and the prescribed amount of the polymerization inhibitor shown in table 1 was added thereto (compounding ratios of each chemical agent was shown below), and highly purified nitrogen gas was injected therein for 30 minutes to remove the dissolved oxygen. Then, the resultant mixture was kept at 120° C. A part of the content therein was taken out as sampling at a given time to measure the amount (ppm) of polymer formed in the liquid. A 9 times volume of methanol based on the sampling liquid was added thereto to precipitate the formed polymer in a suspended state, which was filtrated out to weigh its weight amount and its formed amount (%) in the monomer was evaluated. Incidentally, before the beginning of this test, styrene monomer was washed with an alkali to remove the polymerization inhibitor (tert-butyl catechol) contained in the monomer, washed with water and dried. The results are summarized in table 1.

TABLE 1

| Example | No. | (A) Nitrogeneous Aromatic Compound And Amount Added (ppm) | (B) Sulfonic Acid Compound And Amount Added (ppm) | Amount of Polymer formed (ppm) | | |
|---|---|---|---|---|---|---|
| | | | | After 30 min. | After 60 min. | After 120 min. |
| Working Example | 1 | A-1: 100 | B-1: 100 | 2087 | 2987 | 3740 |
| | 2 | A-2: 100 | B-1: 100 | 0 | 0 | 1331 |

TABLE 1-continued

| Example | No. | (A) Nitrogeneous Aromatic Compound And Amount Added (ppm) | (B) Sulfonic Acid Compound And Amount Added (ppm) | Amount of Polymer formed (ppm) After 30 min. | After 60 min. | After 120 min. |
|---|---|---|---|---|---|---|
| | 3 | A-3: 100 | B-1: 100 | 87 | 341 | 11107 |
| | 4 | A-4: 100 | B-1: 100 | 3471 | 7787 | 12361 |
| | 5 | A-5: 100 | B-1: 100 | 0 | 1231 | 3771 |
| | 6 | A-2: 10 | B-1: 190 | 1230 | 3210 | 6546 |
| | 7 | A-2: 40 | B-1: 160 | 950 | 2010 | 5642 |
| | 8 | A-2: 60 | B-1: 140 | 0 | 268 | 3210 |
| | 9 | A-2: 140 | B-1: 60 | 0 | 521 | 2210 |
| | 10 | A-2: 160 | B-1: 40 | 222 | 1125 | 2642 |
| | 11 | A-2: 190 | B-1: 10 | 320 | 2846 | 3719 |
| | 12 | A-2: 100 | B-2: 100 | 0 | 0 | 1667 |
| | 13 | A-2: 100 | B-3: 100 | 0 | 45 | 2350 |
| | 14 | A-2: 100 | B-4: 100 | 0 | 0 | 1024 |
| | 15 | A-2: 100 | B-5: 100 | 0 | 59 | 1880 |
| | 16 | A-2: 100 | B-6: 100 | 0 | 0 | 2129 |
| | 17 | A-2: 100 | B-7: 50 | 66 | 112 | 6231 |
| | 18 | A-6: 100 | B-1: 100 | 428 | 1159 | 3344 |
| | 19 | A-6: 100 | B-2: 100 | 437 | 1182 | 3411 |
| | 20 | A-6: 100 | B-3: 100 | 514 | 1391 | 4013 |
| | 21 | A-6: 100 | B-4: 100 | 522 | 1414 | 4080 |
| | 22 | A-6: 100 | B-5: 100 | 432 | 1171 | 3377 |
| | 23 | A-6: 100 | B-6: 100 | 471 | 1275 | 3678 |
| | 24 | A-6: 100 | B-7: 50 | 488 | 1722 | 4312 |
| | 25 | A-7: 100 | B-1: 100 | 400 | 1250 | 3641 |
| | 26 | A-6: 10 | B-1: 190 | 1620 | 3260 | 6621 |
| | 27 | A-6: 40 | B-1: 160 | 578 | 1720 | 4121 |
| | 28 | A-6: 60 | B-1: 140 | 523 | 1530 | 3821 |
| | 29 | A-6: 140 | B-1: 60 | 628 | 1239 | 3662 |
| | 30 | A-6: 160 | B-1: 40 | 1738 | 3487 | 7021 |
| | 31 | A-6: 190 | B-1: 10 | 1923 | 3861 | 7822 |
| | 32 | A-8: 100 | B-1: 100 | 3028 | 5577 | 10120 |
| | 33 | A-9: 100 | B-1: 100 | 3120 | 4979 | 8143 |
| | 34 | A-10: 100 | B-1: 100 | 151 | 163 | 248 |
| | 35 | A-11: 100 | B-1: 100 | 2128 | 3549 | 7248 |
| | 36 | A-12: 100 | B-1: 100 | 1720 | 2649 | 5439 |
| | 37 | A-10: 100 | B-1: 200 | 66 | 97 | 101 |
| | 38 | A-10: 50 | B-1: 50 | 1680 | 2939 | 4492 |
| | 39 | A-10: 10 | B-1: 190 | 2890 | 4471 | 7022 |
| | 40 | A-10: 40 | B-1: 160 | 110 | 135 | 212 |
| | 41 | A-10: 160 | B-1: 40 | 98 | 120 | 144 |
| | 42 | A-10: 190 | B-1: 10 | 3011 | 5670 | 11089 |
| | 43 | A-10: 100 | B-2: 100 | 140 | 246 | 377 |
| | 44 | A-10: 100 | B-3: 100 | 162 | 166 | 180 |
| | 45 | A-10: 100 | B-4: 100 | 177 | 189 | 308 |
| | 46 | A-10: 100 | B-5: 100 | 159 | 185 | 233 |
| | 47 | A-10: 100 | B-6: 100 | 153 | 166 | 278 |
| | 48 | A-10: 100 | B-7: 50 | 411 | 450 | 472 |
| Comparative Example | 1 | DNBP: 250 | None | 1896 | 4929 | 16072 |
| | 2 | H-TEMPO: 250 | None | 0 | 0 | 42054 |
| | 3 | A-1: 200 | None | 38344 | — | — |
| | 4 | A-2: 200 | None | 38791 | — | — |
| | 5 | A-3: 200 | None | 34675 | — | — |
| | 6 | A-4: 200 | None | 35681 | — | — |
| | 7 | A-5: 200 | None | 32698 | — | — |
| | 8 | A-6: 200 | None | 38344 | — | — |
| | 9 | A-7: 200 | None | 39463 | — | — |
| | 10 | A-10: 200 | None | 38385 | — | — |
| | 11 | A-11: 200 | None | 39870 | — | — |
| | 12 | A-12: 200 | None | 40010 | — | — |
| | 13 | None | B-1: 200 | 30700 | — | — |
| | 14 | None | B-2: 200 | 31314 | — | — |
| | 15 | None | B-3: 200 | 36840 | — | — |
| | 16 | None | B-4: 200 | 37454 | — | — |
| | 17 | None | B-5: 200 | 31007 | — | — |
| | 18 | None | B-6: 200 | 33770 | — | — |

It can be understood from the results shown in table 1 that by combining the nitrogenous aromatic compound of the (A) component and the sulfonic acid compound of the (B) component the synergic polymerization-inhibiting effect may be exerted and the polymerization-inhibiting effect may be kept over a long period time while when each of them was used singly, almost no appreciable polymerization-inhibiting effect may be obtained.

What is claimed is:

1. A process for inhibiting polymerization of styrene or a styrene derivative having a polymerizable vinyl group which comprises adding a polymerization inhibitor composition consisting essentially of component (A) a nitrogenous aromatic compound represented by the following general formula (III) in combination with component (B) a sulfonic acid compound represented by the following general formula (V) during the stage of producing, purifying, storing or transporting of the styrene or styrene derivative Chemical Formula 3

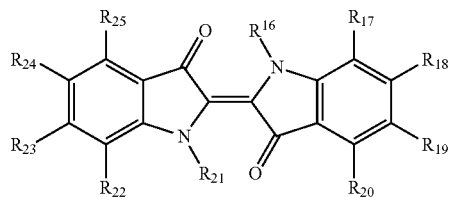

(III)

wherein $R_{16}$-$R_{25}$ represent independently hydrogen, hydroxyl group, a straight or branched chain alkyl group having from 1 to 12 carbon atoms, a straight or branched chain alkenyl group having from 2 to 12 carbon atoms, an aryl group having from 6 to 14 carbon atoms, an amino group, mono- or di-alkyl amino group whose alkyl group is a straight or branched chain having from 1 to 12 carbon atoms, a mono- or di-aryl amino group whose aryl group has from 6 to 12 carbon atoms, a formyl group, a carboxyl group, a carbamoyl group and a sulfonic acid residue, and adjacent two substituent groups may take an alicyclic or an aromatic cyclic structure together, and Chemical Formula 5

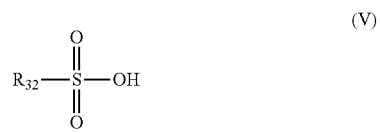

(V)

wherein $R_{32}$ represents a hydroxyl group, a straight or branched chain alkyl group having 1-32 carbon atoms, an alkylphenyl group wherein the alkyl group is a straight or branched chain alkyl having 1-32 carbon atoms or an alkylnaphthyl group wherein the alkyl group is a straight or branched chain alkyl having 1-32 carbon atoms.

2. The process as claimed in claim 1, wherein the nitrogenous aromatic compound represented by the general formula (III) in the before-described (A) component is indigo and/or indigo carmine.

3. The process as claimed in claim 1, wherein the sulfonic acid compound represented by the general formula (V) in the before-described (B) component is at least one member selected from toluenesulfonic acid, xylenesulfonic acid, cumenesulfonic acid, dodecylbenzene sulfonic acid, pentadecylbenzenesulfonic acid and dinonylnaphthalenesulfonic acid.

4. The process as claimed in claim 1, wherein the nitrogenous aromatic compound of the (A) component and the sulfonic acid compound of the (B) component are added in combination in the range of 5:95 to 95:5 by weight ratio.

5. The process as claimed in claim 1, wherein the sulfonic acid compound is selected from the group consisting of dodecylbenzenesulfonic acid, pentadecylbenzenesulfonic acid, xylenesulfonic acid, cumenesulfonic acid, p-toluenesulfonic acid, methanesulfonic acid and sulfuric acid, the nitrogenous aromatic compound being added in an amount of from 10-190 ppm and the sulfonic acid compound being added in an amount of from 10-200 ppm, based on the aromatic vinyl compound.

6. The process as claimed in claim 1, wherein the polymerization inhibitor consists of components (A) and (B).

\* \* \* \* \*